Figure 1:
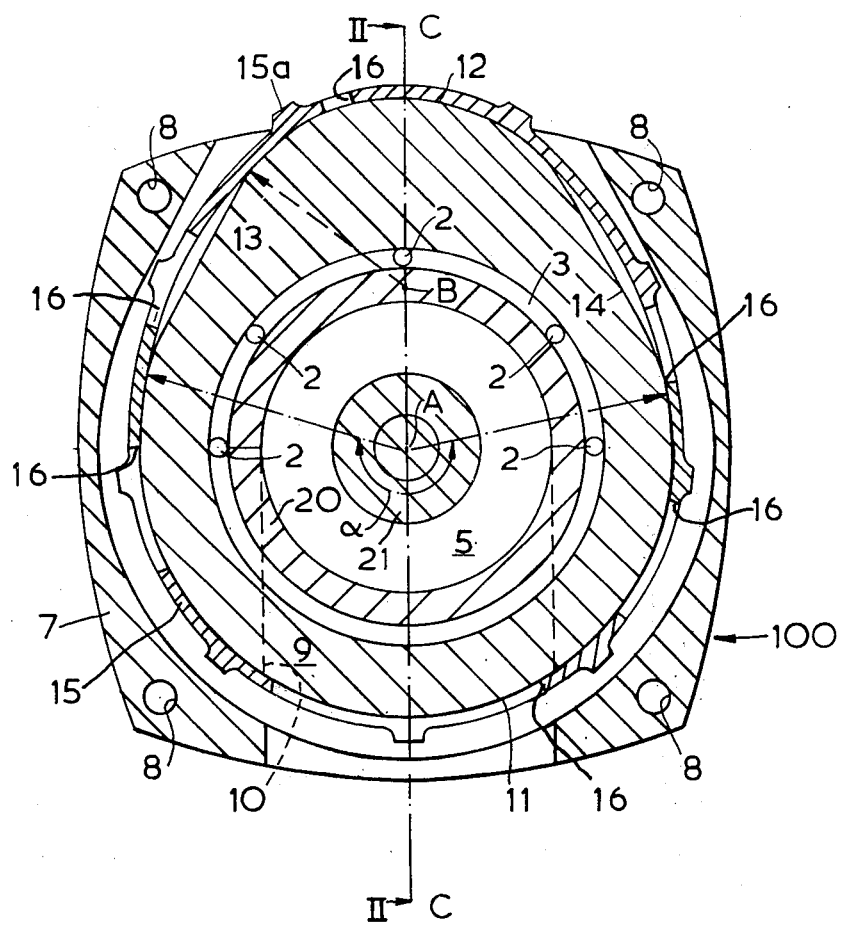

United States Patent
Kernot

[11] 3,990,678
[45] Nov. 9, 1976

[54] AIR FLOW CONTROL DEVICE

[75] Inventor: Ian Dudley Kernot, Skipton, England

[73] Assignee: Cyprane Limited, England

[22] Filed: Sept. 23, 1975

[21] Appl. No.: 616,061

Related U.S. Application Data

[63] Continuation-in-part of Ser. No. 514,445, Oct. 15, 1974, abandoned.

[30] Foreign Application Priority Data

Oct. 18, 1973   United Kingdom............... 48649/73

[52] U.S. Cl............................. 251/208; 251/DIG. 2; 251/345
[51] Int. Cl.²......................................... F16K 3/28
[58] Field of Search.............. 251/DIG. 2, 344, 345, 251/343, 208

[56] References Cited
UNITED STATES PATENTS

| | | | |
|---|---|---|---|
| 1,272,950 | 7/1918 | Hawkins | 251/345 |
| 2,839,080 | 6/1958 | Copeland | 251/345 |
| 3,039,463 | 6/1962 | Dickey Jr. | 251/345 X |
| 3,135,293 | 6/1964 | Hulsey | 251/345 X |

FOREIGN PATENTS OR APPLICATIONS

705,690   3/1965   Canada.............. 251/DIG. 2

*Primary Examiner*—Arnold Rosenthal
*Attorney, Agent, or Firm*—Jay L. Chaskin

[57] ABSTRACT

Air flow control means comprising a substantially annular member having an outer surface and an inner surface, a port formed through said member and connecting said surfaces, a flexible, resilient band having at least one passage therethrough, said band surrounding and slidable on said outer surface and the shape of said outer surface being such that said band follows a path that is spaced from said outer surface in at least two spaced-apart regions thereof and contacts said outer surface in at least two further regions thereof, one of said further regions being the region of said port, the distortion of said band being such that said band is pulled into sealing engagement with said outer surface in the region of said port.

4 Claims, 2 Drawing Figures

AIR FLOW CONTROL DEVICE

This application is a continuation-in-part of application Ser. No. 514,445, filed Oct. 15, 1974, and now abandoned, which claims the priority of British Application No. 48649/73, filed Oct. 18, 1973.

This invention relates to means for controlling the flow of air into a system. There are many fields wherein a controlled intake of air is required, and the object of the invention is to provide a control means which is simple to manufacture, light in weight and accurate.

In accordance with the invention air flow control means comprises a substantially annular member having an outer surface and an inner surface, a port formed through said member and connecting said surfaces, a flexible, resilient band having at least one passage therethrough, said band surrounding and slidable on said outer surface and the shape of said outer surface being such that said band follows a path that is spaced from said outer surface in at least two spaced-apart regions thereof and contacts said outer surface in at least two further regions thereof, one of said further regions being the region of said port, the distortion of said band being such that said band is pulled into sealing engagement with said outer surface in the region of said port.

By sliding the band around the outer surface of the annular member the port can be occluded as desired so that the area available for air flow is determined by the cross-section of the passage or section of passages that overlies the port. The distortion of the band is effective to create the required sealing effect in the region of the port while still allowing the band to be slidable around the surface. Preferably a number of separate passages of different areas are formed through the band, although it is possible to form the band with a single passage, the width of which varies along the length of the band.

When seen in transverse cross-section said outer surface may be non-circular and said band when removed from said outer surface and in its relaxed condition may be circular.

In transverse cross-section the outer surface of the member may define a first part-circular arc subtending an angle of more than 180° at the centre from which the arc is drawn, a second part-circular arc drawn about a different centre and to a smaller radius than the first arc, and straight lines joining and tangential to the two arcs, the surface being symmetrical about a line joining the centres from which the two arcs are drawn. A flexible band placed around this surface will run in contact with the two arcuate sections but will not contact the two straight-line sections of the surface.

Figure 2:
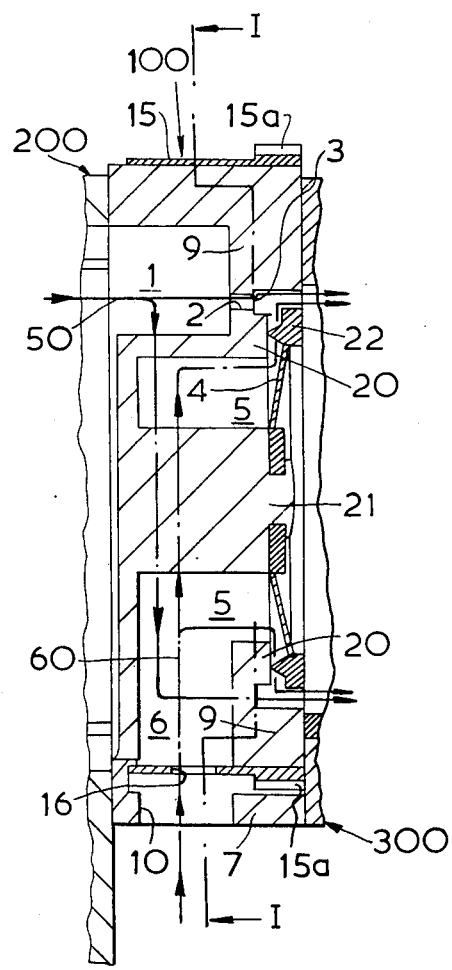

A specific embodiment of air flow control means according to the invention will now be described in more detail, by way of example only, with reference to the accompanying drawings in which:

FIG. 1 is a transverse cross-section through the device, on line I—I on FIG. 2; and FIG. 2 is a cross-section on the line II—II of FIG. 1.

The device 100 shown is for use in apparatus used for inhalation therapy and patient-administered analgesia, and forms one module of a complete assembly for supplying oxygen or other gas to a patient in admixture with air, in response to suction applied by the patient to an outlet from module 300. Parts of other modules of the assembly are indicated as 200 and 300 in FIG. 2, and the assembly may generally be as disclosed in application Ser. No. 514,763 filed by David Allan Needham on Oct. 15, 1974 and assigned to the same assignee of record, the entire contents of which are hereby incorporated by reference. The inlet side of the device has a part-circular channel 1 to which gas is supplied and may pass through passages 2 to an annular groove 3 on the outlet side of the device, the flow path of the gas being indicated by arrow 50.

The body of the device is conveniently moulded from a plastics material and, as seen in FIG. 1, it comprises a horseshoe shaped outer section 7 having bolt holes 8 extending through the full thickness of the body whereby the device may be bolted to the adjoining modules 200 and 300. Within the outer section 7 is a substantially annular member 9 having an outer surface extending substantially the full thickness of the body and interrupted only by an air port 10 leading to an inner surface 10a of member 9, which inner surface surrounds an air intake chamber 6. The outer surface of the member 9, as seen in cross-section in FIG. 1 is made up of a first circular arc 11 subtending an angle $\alpha$ (greater than 180°) at the centre A from which the arc is drawn, a second circular arc 12 of smaller radius than the first one and drawn from a different centre B, and two straight lines 13, 14 joining and tangential to the two arcs. The surface is symmetrical about a line C—C joining the two centres.

Within the substantially annular member 9 the body defines an annular valve seat 20, and within the annular valve seat 20 the body defines a central boss 21. The valve seat 20 is spaced from the boss 21 by an annular part 5 communicating with the air intake chamber 6. A diaphragm-type non-return valve 4 is secured to the boss 21 by springing a resilient ring 4a over an enlarged head 21a projecting from the boss, and the sealing member 22 of the valve 4 seals against the valve seat 20.

Passing around the outer surface of the member 9 is a flexible, resilient band 15, preferably of plastics material, which lies in contact with the arcuate sections 11 and 12 but is spaced from the two straight line sections 13, 14. When removed from the member 9 the relaxed shape of the band 15 is substantially circular. The distortion of the band when it is forced on to the member in push-fit relation thereto leads to an effective seal being made around the port 10, and yet allows the band to slide around the surface by application of a suitable force. The outer face of the band is formed with a series of spaced, transversely extending ridges 15a which may be manually engaged to move the belt around the surface. A number of passages 16 of equal width and all rectangular in cross-section are formed through the band. As shown in FIG. 1 all the passages are of different lengths and they are thus of different areas. Any selected passage can be brought to overlie the port by appropriate rotation of the band. The area available for air to flow through into chamber can thus be changed and the invention provides a simple device for controlling air flow. The flow of air through the device is indicated by the arrow 60.

In use, a patient applies suction to module 300, and the suction effect lifts the sealing member 22 of the valve 4 from the seat 20 and draws air past the valve 4 from the annular part 6. The air flow through the device is from atmosphere through air part 10 and the selected passage 16 through band 15 to air intake chamber 6, thence to annular part 5 and past the valve 4 to module 300 and so to the patient. The air flowing past the valve 4 passes the groove 3 and this movement creates a pressure reduction at the groove. The effect of this reduction and of the patient applied suction is to draw gas from the module 200 to channel 1 and through passages 2 to groove 3 from whence the gas is admixed with the air and delivered to module 300 and so to the patient. By controlling the incoming air flow by appropriate selection of the desired passage 16 the gas/air mixture and total flow through the device can be regulated as required.

In modified forms of the apparatus the passages need not be rectangular in cross-section, but may be circular, polygonal or of any other shape and the shape of different passages need not be similar. In another alternative the flexible band 15 has a single passage therethrough, and the width of the passage varies along the length of the band.

Obviously the device is not limited to use in inhalation therapy equipment, nor is the invention limited to the particular configuration of parts shown in the drawings.

What I claim is:

1. Air flow control means comprising a substantially annular member having an outer surface and an inner surface, a port formed through said member and connecting said surfaces, a flexible, resilient band having at least one passage therethrough, said band surrounding and slidable on said outer surface and the shape of said outer surface being such that said band follows a path that is spaced from said outer surface in at least two spaced-apart regions thereof and contacts said outer surface in at least two further regions thereof, one of said further regions being the region of said port, the distortion of said band being such that said band is pulled into sealing engagement with said outer surface in the region of said port.

2. Air flow control means as claimed in claim 1 wherein said outer surface when seen in transverse cross-section is non-circular and said band when removed from said outer surface and in its relaxed condition is substantially circular in transverse cross-section.

3. Air flow control means as claimed in claim 1 wherein a plurality of separate passages each of different area are formed through said flexible band.

4. Air flow control means as claimed in claim 1, wherein said outer surface of said substantially annular member defines, in transverse cross-section, a first partcircular arc subtending an angle of not less than 180° at the centre from which the arc is drawn, a second partcircular arc drawn about a different centre and to a smaller radius than the first arc, and straight lines joining and substantially tangential to said two arcs, and said cross-section is symmetrical about a line joining said centres from which said two arcs are drawn.

* * * * *